United States Patent
Pennoyer et al.

(10) Patent No.: US 11,039,897 B2
(45) Date of Patent: *Jun. 22, 2021

(54) DRAPE MANAGEMENT ASSEMBLIES FOR ROBOTIC SURGICAL SYSTEMS

(71) Applicant: Covidien LP, Mansfield, MA (US)

(72) Inventors: Raymond Pennoyer, Berlin, CT (US); Eric Meade, Pocasset, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/794,726

(22) Filed: Feb. 19, 2020

(65) Prior Publication Data

US 2020/0179072 A1    Jun. 11, 2020

Related U.S. Application Data

(63) Continuation of application No. 16/077,500, filed as application No. PCT/US2017/019237 on Feb. 24, 2017, now Pat. No. 10,736,707.

(60) Provisional application No. 62/300,147, filed on Feb. 26, 2016.

(51) Int. Cl.

| A61B 46/10 | (2016.01) |
| A61B 34/35 | (2016.01) |
| A61B 34/30 | (2016.01) |
| A61B 17/00 | (2006.01) |

(52) U.S. Cl.
CPC ............ *A61B 46/10* (2016.02); *A61B 34/35* (2016.02); *A61B 34/30* (2016.02); *A61B 2017/0023* (2013.01); *A61B 2017/00477* (2013.01)

(58) Field of Classification Search
CPC ......... A61B 46/10; A61B 46/23; A61B 34/30; A61B 34/35; A61B 2017/0023; A61B 2017/00477
See application file for complete search history.

(56) References Cited

U.S. PATENT DOCUMENTS

| 6,123,080 | A | 9/2000 | Mohan et al. |
| 6,132,368 | A | 10/2000 | Cooper |
| 9,259,277 | B2 | 2/2016 | Rogers et al. |
| 10,736,707 | B2 * | 8/2020 | Pennoyer ............... A61B 46/10 |
| 2010/0292707 | A1 | 11/2010 | Ortmaier et al. |
| 2010/0319713 | A1 | 12/2010 | Byers et al. |
| 2012/0116416 | A1 | 5/2012 | Neff et al. |
| 2014/0069436 | A1 | 3/2014 | Khalil et al. |
| 2014/0261456 | A1 | 9/2014 | Malackowski et al. |
| 2015/0202009 | A1 | 7/2015 | Nussbaumer et al. |

(Continued)

FOREIGN PATENT DOCUMENTS

WO    2015142824 A1    9/2015

OTHER PUBLICATIONS

European Office Action dated Aug. 6, 2020 corresponding to counterpart Patent Application EP 17 757 252.6.

(Continued)

*Primary Examiner* — Dean J Kramer

(57) ABSTRACT

A drape management assembly for a robotic surgical system includes a base portion and a grasping portion. The base portion is configured for connection to the robotic surgical system. The grasping portion extends from the base portion and defines a cavity therebetween. The cavity is configured to locate an excess portion of a drape which sheaths at least a robotic arm of the robotic surgical system.

16 Claims, 4 Drawing Sheets

(56) References Cited

U.S. PATENT DOCUMENTS

2015/0366618 A1    12/2015   Higuchi et al.
2015/0374445 A1    12/2015   Gombert et al.
2018/0200014 A1     7/2018   Bonny et al.

OTHER PUBLICATIONS

Chinese First Office Action dated Sep. 10, 2020 corresponding to counterpart Patent Application CN 201780012726.9.
International Search Report and Written Opinion corresponding to counterpart Int'l Appln. No. PCT/US2017/019237 dated Jun. 2, 2017.
Extended European Search Report dated Sep. 2, 2019 corresponding to counterpart Patent Application EP 17757252.6.

* cited by examiner

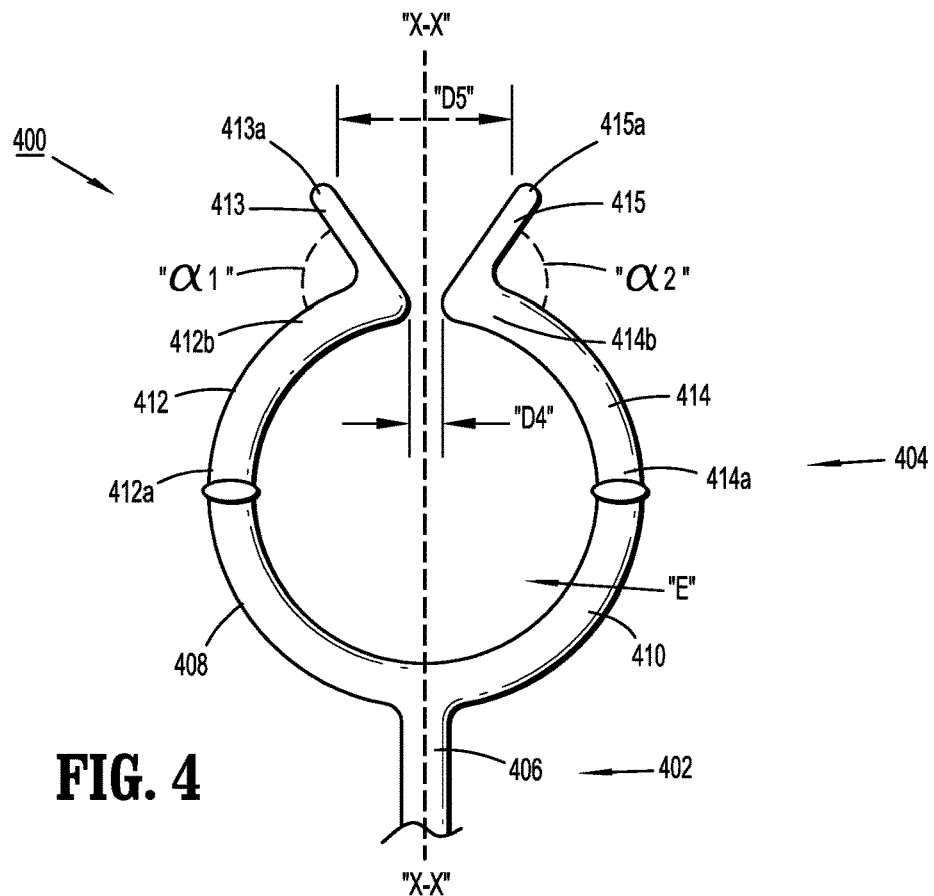
FIG. 4
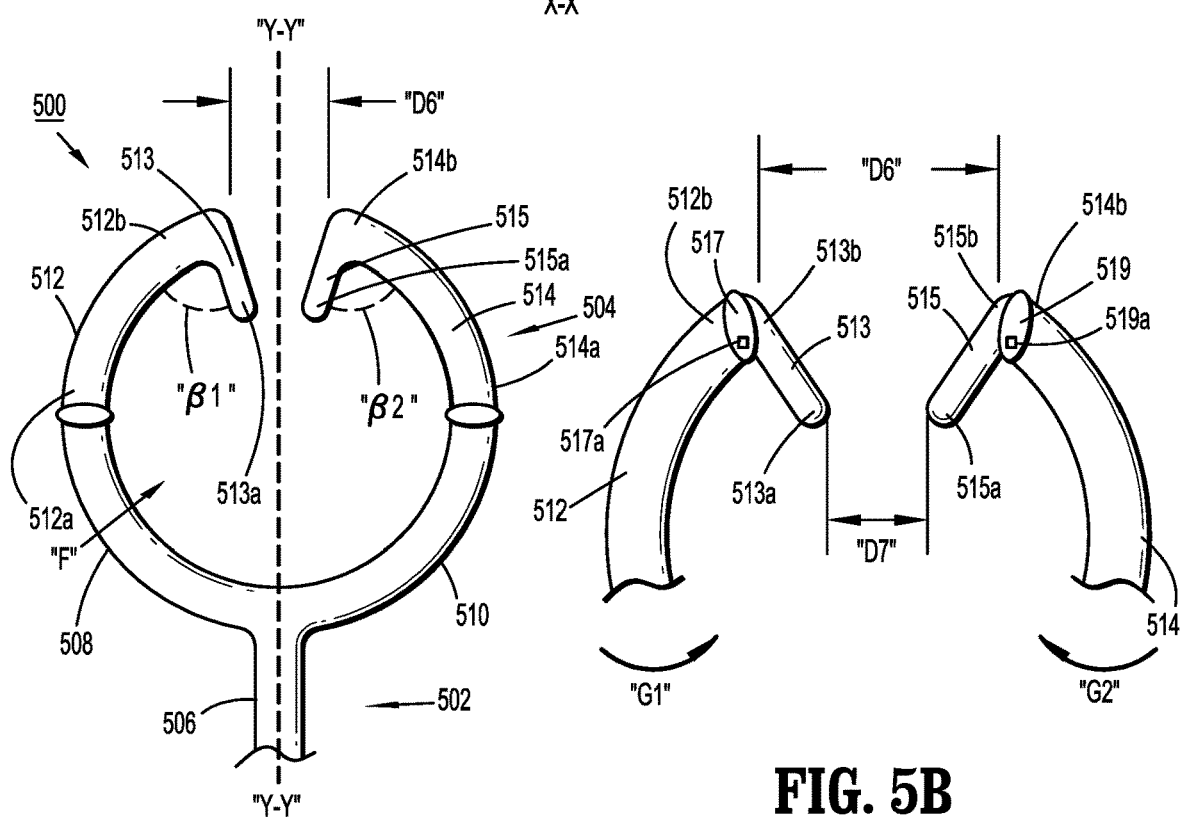
FIG. 5A
FIG. 5B

DRAPE MANAGEMENT ASSEMBLIES FOR ROBOTIC SURGICAL SYSTEMS

CROSS-REFERENCE TO RELATED APPLICATIONS

This application is a Continuation Application which claims the benefit of and priority to U.S. patent application Ser. No. 16/077,500, filed on Aug. 13, 2018, which is a U.S. National Stage Application filed under 35 U.S.C. § 371(a) of International Patent Application Serial No. PCT/US2017/019237, filed Feb. 24, 2017, which claims the benefit of and priority to U.S. Provisional Patent Application Ser. No. 62/300,147, filed Feb. 26, 2016, the entire disclosure of each of which being incorporated by reference herein.

BACKGROUND

Robotic surgical systems have been used in minimally invasive medical procedures. Some robotic surgical systems include a console supporting a robotic arm, and a robotic surgical instrument having at least one end effector such as forceps or a grasping tool that is mounted to the robotic arm via a wrist assembly. Cables extend from the console, through the robotic arm, and connect to the wrist assembly and/or end effector to provide mechanical power to the end effector for its operation and movement.

During a medical procedure, the end effector and the wrist assembly are inserted into a small incision (via a cannula) or a natural orifice of a patient to position the end effector at a work site within the body of the patient. In order to establish and maintain a sterile barrier between the patient, a surgical field, and/or the robotic surgical system, a drape or the like may be used to enclose a portion of the robotic surgical system.

However, it is often the case that excess draping material and/or cables may interfere with the medical procedure by interfering with a movement of the robotic arm or robotic surgical instrument and/or getting in the way of medical personnel.

Accordingly, a need exists for a way to contain excess draping material and route the cables to keep one or both out of the way during a medical procedure or to more efficiently route the same.

SUMMARY

In accordance with an aspect of the present disclosure, a drape management assembly for a robotic surgical system is provided. The drape management assembly includes a base portion and a grasping portion. The base portion is configured for connection to the robotic surgical system. The grasping portion extends from the base portion and defines a cavity therebetween. The cavity is configured to locate an excess portion of a drape which sheaths at least a robotic arm of the robotic surgical system.

In some embodiments, the grasping portion may include a first jaw and second jaw each rotatably coupled to the base portion. In a first configuration, the first and second jaws may be rotatably approximated and in a second configuration, the first and second jaws may be rotatably spaced apart.

It is contemplated that the first and second jaws may be resiliently biased to rotatably return to the first configuration.

It is envisioned that the base portion may include a first prong and a second prong. The first prong may operably support the first jaw and the second prong may operably support the second prong.

In some aspects of the present disclosure, each of the first and second jaws may include a first and second end, respectively, wherein the first end of each of the first and second jaws may be hingedly coupled to the first and second prongs, respectively.

In some embodiments, in the first configuration, the second ends of the first and second jaws may be spaced apart a first distance, and in the second configuration, the second ends of the first and second jaws may be spaced apart a second distance greater than the first distance.

It is envisioned that the cavity may include a first cavity formed by the base portion and the grasping portion in the first configuration, and a second cavity formed by the base portion and the grasping portion in the second configuration, the second cavity being larger than the first cavity.

It is contemplated that the first and second prongs may each include a first radius of curvature and the first and second jaws may each include a second radius of curvature.

In some aspects of the present disclosure, the base portion may further include a stem supporting the first and second prongs.

In some embodiments, in the first configuration, the first distance between the second ends of the first and second jaws may be configured to incrementally release the excess portion of the drape from within the cavity formed by the base portion and the grasping portion.

It is envisioned that in the second configuration, the second distance between the second ends of the first and second jaws may be configured for gathering and locating the excess portion of the drape within the cavity formed by the base portion and the grasping portion such that the excess portion of the drape is located and captured within the cavity formed by the base portion and the grasping portion when the first and second jaws are returned to the first configuration.

It is contemplated that the drape management assembly may further include a securing member configured to selectively fix the first and second jaws in the second configuration.

In some aspects of the present disclosure, the second ends of the first and second jaws may each include a first and second lip, respectively, wherein the first and second lips may each include an end portion extending away from the second ends of the first and second jaws.

In some embodiments, the first and second lips may extend away from the cavity formed by the base portion and the grasping portion and away from one another, such that a distance between the end portions of the first and second lips is greater than a distance between the second ends of the first and second jaws.

It is envisioned that the first and second lips may extend towards the cavity formed by the base portion and the grasping portion and towards one another, such that a distance between the end portions of the first and second lips is less than a distance between the second ends of the first and second jaws.

It is contemplated that the first and second lips may be hingedly coupled to the second ends of the first and second jaws respectively, and resiliently biased to an approximated position wherein the distance between the end portions thereof is less than the distance between the second ends of the first and second jaws.

In another aspect of the present disclosure, a drape management assembly for a robotic surgical system is provided. The drape management assembly includes a base portion and a grasping portion. The base portion includes a first prong having a first end and a second end and a second prong having a first end and a second end, the first and second prongs coupled to one another at the respective first ends thereof. The grasping portion includes a first jaw having a first end and a second end and a second jaw having a first end and a second end, the first ends of the first and second jaws operably coupled to the second ends of the first and second prongs, respectively. The base portion and the grasping portion define a cavity therebetween, wherein the cavity is configured to locate an excess portion of a drape.

In some embodiments, the drape management assembly may further include a first hinge rotatably coupling the first prong and the first jaw and a second hinge rotatably coupling the second prong and the second jaw. The first and second hinges may be spring loaded such that the first and second jaws are resiliently biased to a first configuration wherein the second ends of the first and second jaws are approximated.

It is contemplated that the drape may be configured to enclose a robotic arm of the robotic surgical system, and the drape management assembly may be configured to incrementally release the excess drape portion such that the robotic arm maintains a full range of motion while enclosed within the drape.

It is envisioned that the base portion may include a stem having a threaded portion configured to threadably couple the drape management assembly to a robotic arm of the robotic surgical system.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIG. 4 is a front view of the drape management assembly of FIG. 1 in accordance with an alternative embodiment of the present disclosure;

FIG. 5A is a front view of the drape management assembly of FIG. 1 in accordance with another alternative embodiment of the present disclosure; and FIG. 5B is a front view of a grasping portion of the drape management assembly of FIG. 5A in accordance with an alternative embodiment of the present disclosure.

DETAILED DESCRIPTION

Figure 1:
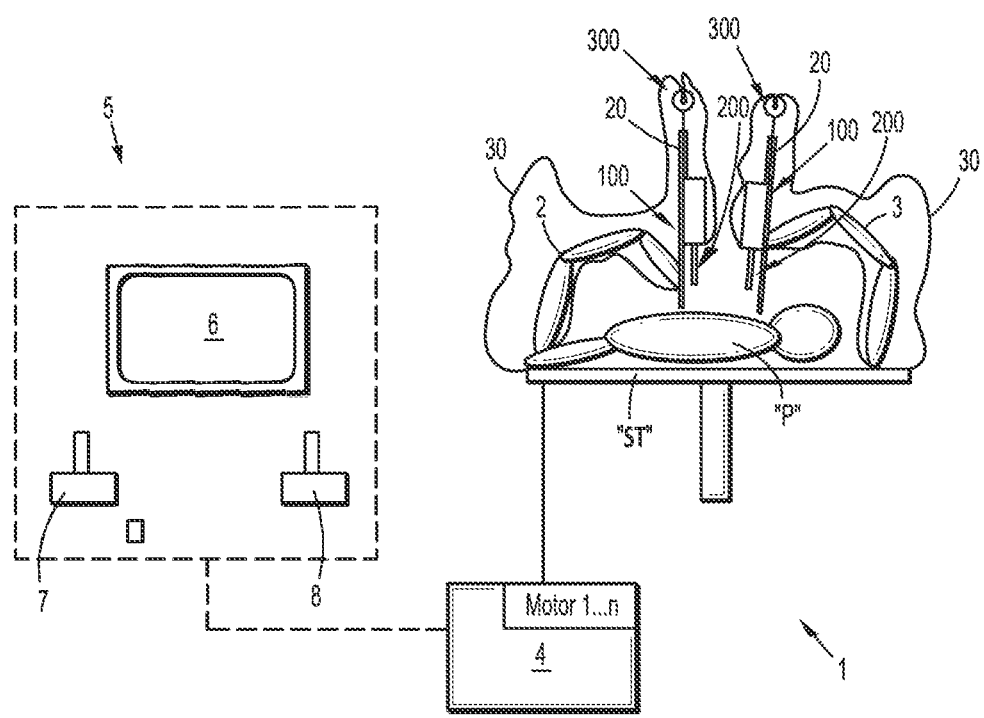
FIG. 1 is a schematic illustration of a robotic surgical system including a drape management assembly in accordance with the present disclosure.

Embodiments of the presently disclosed drape management assembly and methods of use thereof are described in detail with reference to the drawings, in which like reference numerals designate identical or corresponding elements in each of the several views. As used herein the term "distal" refers to that portion of the robotic surgical system, surgical assembly, or component thereof, that is closer to a patient, while the term "proximal" refers to that portion of the robotic surgical system, surgical assembly, or component thereof, that is farther from a patient.

As will be described in detail below, provided is a drape management assembly configured to be attached to a robotic surgical system. The drape management assembly includes a cavity configured to locate an excess portion of a drape as the drape encloses or sheaths a portion of the robotic surgical system, such as, for example, a robotic arm.

Referring initially to FIG. 1, a surgical system, such as, for example, a robotic surgical system 1, generally includes one or more robotic arms 2, 3, a control device 4, and an operating console 5 coupled with control device 4. Robotic arms 2, 3 may each have a robotic surgical assembly 100 and an electromechanical surgical instrument 200 coupled thereto. In some embodiments, robotic surgical assembly 100 may be coupled to a slide rail 20 of robotic arms 2, 3.

Operating console 5 includes a display device 6, which is set up to display three-dimensional images; and manual input devices 7, 8, by means of which a clinician (not shown), is able to telemanipulate robotic arms 2, 3 in a first operating mode, as known in principle to a person skilled in the art. Robotic arms 2, 3 may be driven by electric drives (not shown) that are connected to control device 4 (e.g., a computer) which is set up to activate the drives, for example, by means of a computer program, in such a way that robotic arms 2, 3, the attached robotic surgical assembly 100, and thus electromechanical surgical instrument 200 (including the electromechanical end effector, not shown) execute a desired movement according to a movement defined by means of manual input devices 7, 8. Control device 4 may also be set up in such a way that it regulates the movement of robotic arms 2, 3 and/or of the drives. To that end, control device 4 may control a plurality of motors, e.g., motors (Motor 1 . . . n), with each motor configured to drive movement of robotic arms 2, 3 in a plurality of directions.

Robotic surgical system 1 is configured for use on a patient "P" positioned (e.g., lying) on a surgical table "ST" to be treated in a minimally invasive manner by means of a surgical instrument, e.g., electromechanical surgical instrument 200. The robotic surgical system 1 may also include more than two robotic arms 2, 3, the additional robotic arms likewise connected to control device 4 and telemanipulatable by means of operating console 5. A surgical instrument, for example, electromechanical surgical instrument 200 (including the electromechanical end effector thereof), may also be attached to any additional robotic arm(s).

For a detailed description of the construction and operation of a robotic surgical system, reference may be made to U.S. Patent Application Publication No. 2012/0116416, filed on Nov. 3, 2011 (now U.S. Pat. No. 8,828,023), entitled "Medical Workstation," the entire contents of which are incorporated by reference herein.

Figure 2:
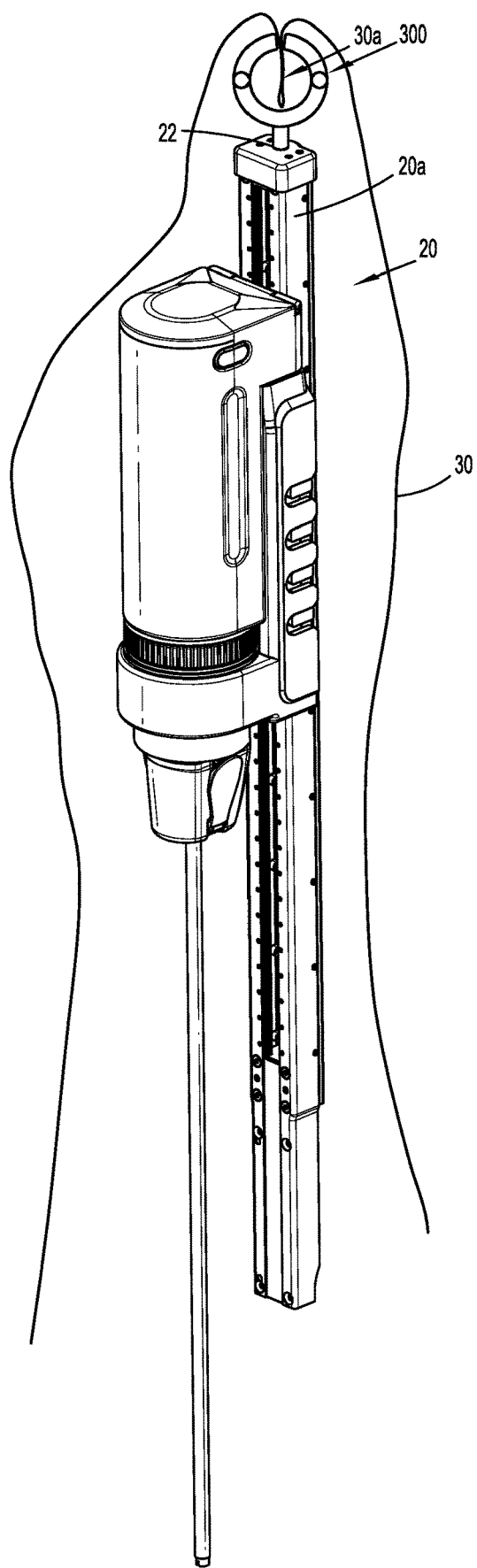
FIG. 2 is a front, perspective view of the drape management assembly of FIG. 1 positioned on a slide rail of a robotic arm and including a drape sheathing the slide rail of the robotic arm.

With continued reference to FIG. 1 and additional reference to FIG. 2, robotic surgical system 1 includes one or more sterile barriers or drapes 30 enclosing robotic arms 2, 3 and robotic surgical assemblies 100 coupled thereto. Drape 30 is configured to create an enclosed sterile environment to prevent contamination of robotic arms 2, 3 and robotic surgical assemblies 100 coupled thereto from, for example, electromechanical surgical instrument 200, bodily fluids, the operating room environment, etc. It is envisioned that drape 30 includes excess draping material or portions to provide enough slack such that the enclosed robotic arms 2, 3 and robotic surgical assemblies 100 coupled thereto maintain operable in a full range of motion while remaining within the sterile enclosure of drape 30. To that end, robotic surgical system 1 includes a drape management assembly 300 configured to control and manage the excess draping material, such as, for example, an excess portion 30a of drape 30, as illustrated in FIGS. 1 and 2.

Figure 3A:
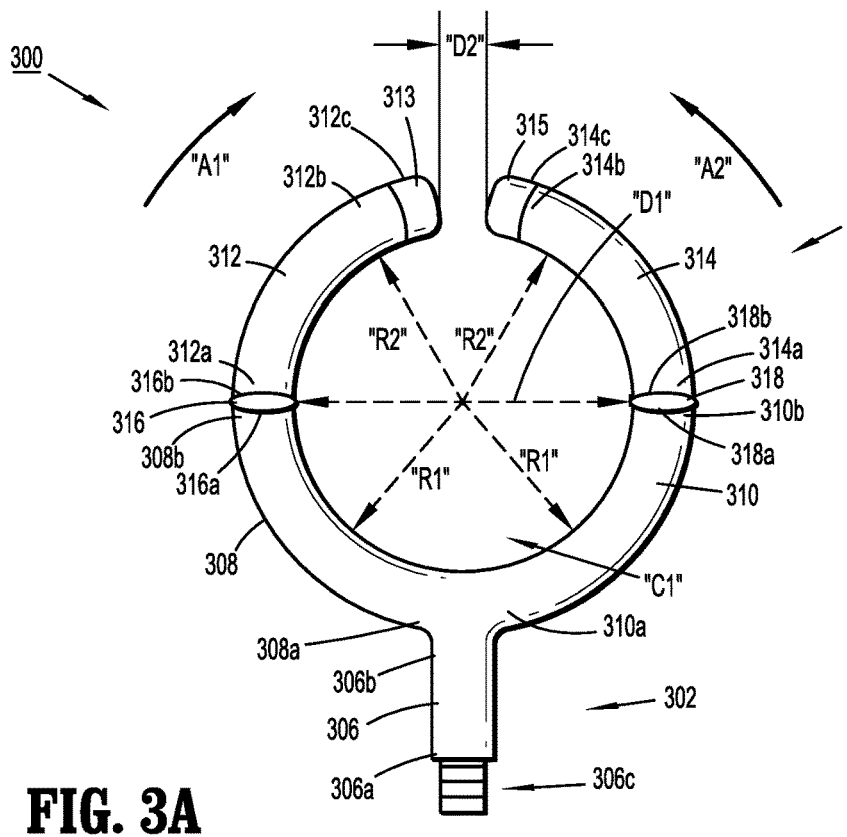
FIG. 3A is a front view of the drape management assembly of FIG. 1 in a first configuration.
Figure 3B:
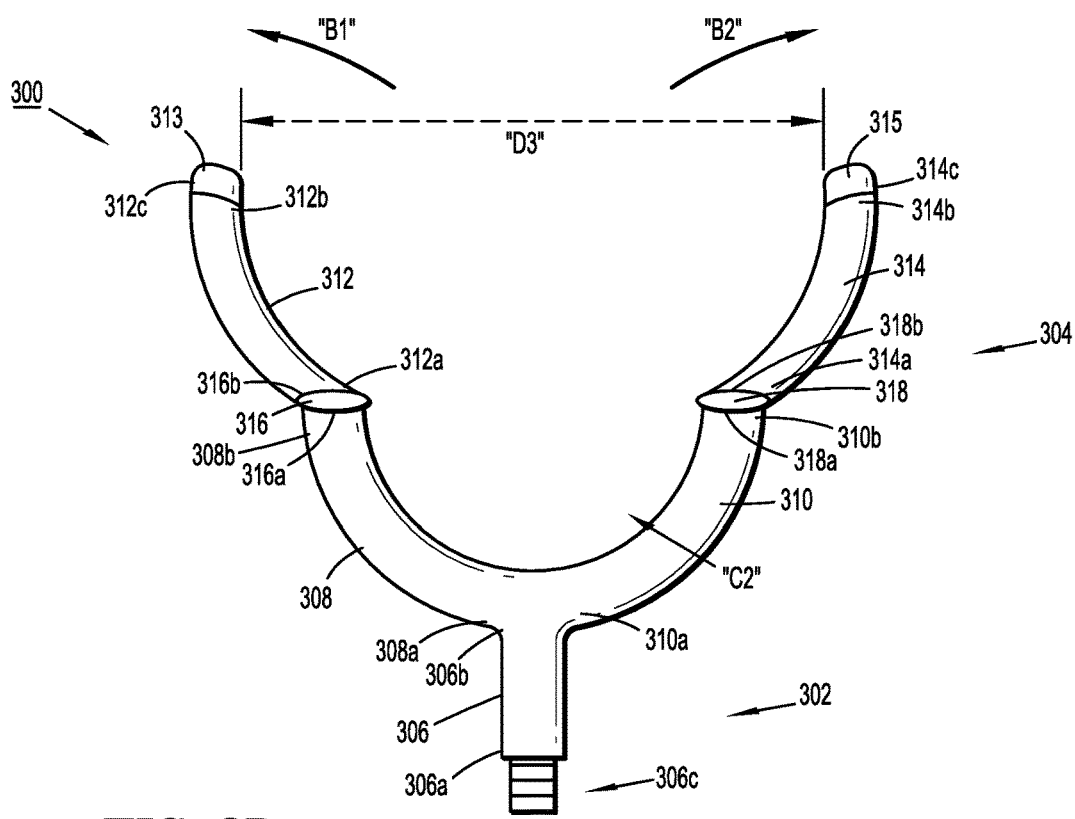
FIG. 3B is a front view of the drape management assembly of FIG. 1 in a second configuration.

With reference to FIG. 2 and additional reference to FIGS. 3A and 3B, in some embodiments, drape management assembly 300 is operably coupled to a first end 20a of slide rail 20 of robotic arms 2, 3. However, in certain embodiments, drape management assembly 300 may be coupled to alternative components of robotic surgical system 1, such as, for example, robotic surgical assembly 100 (not specifically shown).

Drape management assembly 300 includes a first and second configuration as best illustrated in FIGS. 3A and 3B, respectively. Generally, drape management assembly 300 has a base portion 302 and a grasping portion 304 pivotally or hingedly coupled to base portion 302. Base portion 302 includes a stem 306, and a first prong 308 and a second prong 310, each extending from stem 306.

Stem 306 has a first end 306a configured to couple to robotic surgical system 1, such as, for example, rail 20 (see. FIG. 2), and a second end 306b configured to couple to prongs 308, 310. In some embodiments, first end 306a includes a threaded portion 306c configured to be threadably located within a corresponding slot or aperture 22 (see FIG. 2) on first end 20a of slide rail 20 of robotic arms 2, 3 to removably attach drape management assembly 300 to robotic arms 2, 3. Alternatively, in certain embodiments, first end 306a of stem 306 may be fastened to first end 20a of slide rail 20 using adhesives, clips, fasteners or the like. In other embodiments, first end 306a of stem 306 may be monolithically formed with first end 20a of slide rail 20.

Continuing with FIGS. 3A and 3B, prongs 308, 310 each include a first end 308a, 310a and a second end 308b, 310b, respectively, wherein first ends 308a, 310a of prongs 308, 310 are configured to couple to second end 306b of stem 306. In some embodiments, first ends 308a, 310a of prongs 308, 310 are monolithically formed with second end 306b of stem 306. In certain embodiments, first ends 308a, 310a of prongs 308, 310 may be removably attached to second end 306b of stem 306.

Second ends 308b, 310b of prongs 308, 310 are spaced apart by a distance indicated by "D1." In some embodiments, distance "D1" between ends 308b, 310b of prongs 308, 310 is approximately 1.5 inches (3.81 centimeters). However, it is contemplated that distance "D1" may alternatively be any suitable distance.

Prongs 308, 310 are curved such that prongs 308, 310 each include a radius of curvature "R1." In some embodiments, prongs 308, 310 may each include a different radius of curvature (not specifically shown). In certain embodiments, prongs 308, 310 may instead be linear and define an angle (not specifically shown) therebetween. As illustrated in the figures, stem 306 and prongs 308, 310 together define a substantially Y-shaped base portion 302. However, in certain embodiments, base portion 302 may assume a variety of alternative shapes as necessary for its intended purpose.

Grasping portion 304 of drape management assembly 300 includes a first jaw 312 and a second jaw 314. Jaws 312, 314 are pivotally or hingedly coupled to prongs 308, 310 via a first hinge 316 and a second hinge 318, respectively. Jaws 312, 314 each include a first end 312a, 314a and a second end 312b, 314b, respectively, and hinges 316, 318 each include a first portion 316a, 318a and a second portion 316b, 318b, respectively. Second ends 308b, 310b of prongs 308, 310 are configured to be coupled with respective hinges 316, 318 at first portions 316a, 318a thereof. Similarly, first ends 312a, 314a of jaws 312, 314 are configured to be coupled with respective hinges 316, 318 at second portions 316b, 318b thereof. In some embodiments, jaws 312, 314 and prongs 308, 310 are removably attached to respective hinges 316, 318 using fasteners (not shown) such as, for example, pins or the like. In other embodiments, jaws 312, 314 and prongs 308, 310 may be fixedly attached to respective hinges 316, 318 using suitable adhesives, fasteners or the like.

Hinges 316, 318 are spring loaded such that first jaw 312 is resiliently biased in a direction indicated by arrow "A1" and second jaw 314 is resiliently biased in a direction indicated by arrow "A2." In other words, hinges 316, 318 are resiliently biased to return jaws 312, 314 to the first configuration of drape management assembly 300, as illustrated in FIG. 3A, wherein jaws 312, 314 are approximated relative to one another.

In other embodiments, hinges 316, 318 may include shape-memory alloys configured to return jaws 312, 314 to the first configuration of drape management assembly 300, wherein jaws 312, 314 are approximated relative to one another.

In the first configuration, prongs 308, 310 and jaws 312, 314 together, define a cavity "C1" configured to releasably locate excess portion 30a of drape 30. Though jaws 312, 314 are approximated, second ends 312b, 314b of jaws 312, 314 remain spaced apart a distance indicated by "D2." It is contemplated that distance "D2" between second ends 312b, 314b of jaws 312, 314 is sized and configured to substantially retain excess portion 30a of drape 30 within cavity "C1" while incrementally releasing excess portion 30a of drape 30 from within cavity "C1" as necessary to maintain full range of motion for robotic arms 2, 3 and robotic surgical assemblies 100 coupled thereto while remaining within the sterile enclosure of drape 30.

With specific reference to FIG. 3B, in the second configuration of drape management assembly 300, first jaw 312 is rotated about first hinge 316 relative to first prong 308 in a direction indicated by arrow "B1," and second jaw 314 is rotated about second hinge 318 relative to second prong 310 in a direction indicated by arrow "B2." Jaws 312, 314 are both rotated to the second configuration in the directions indicated by arrows "B1" and "B2," respectively, against the resilient bias of hinges 316, 318 in the directions indicated by arrows "A1" and "A2," respectively. Once fully rotated, second ends 312b, 314b of jaws 312, 314 are spaced apart by a distance indicated by "D3," wherein distance "D3" is greater than distance "D2" between second ends 312b, 314b of jaws 312, 314, when in the first configuration. In the second configuration, prongs 308, 310 and jaws 312, 314 define a cavity "C2" therebetween wherein cavity "C2" is larger than cavity "C1" defined by prongs 308, 310 and jaws 312, 314 in the first configuration. Distance "D3" between second ends 312b, 314b of jaws 312, 314 is sized and configured to enable a clinician to gather and locate excess portion 30a of drape 30 within cavity "C2" such that excess portion 30a of drape 30 may be captured and located within cavity "C1" when jaws 312, 314 are returned to the first configuration.

In some embodiments, hinges 316, 318 may each include a securing member or a hinge lock (not shown), wherein the hinge locks are configured to selectively fix jaws 312, 314 in the second configuration.

Though not specifically shown in the figures, in certain embodiments, it is contemplated that jaws 312, 314 may share a common hinge, wherein jaws 312, 314 are hingedly coupled to the common hinge at second ends 312b, 314b thereof. In other embodiments, it is contemplated that one of jaws 312, 314 may be fixed while the other is rotatable.

Returning briefly to FIG. 3A, similar to prongs 308, 310, jaws 312, 314 are curved such that jaws 312, 314 each include a radius of curvature "R2," wherein radius of curvature "R2" is equal to radius of curvature "R1" defined by prongs 308, 310. As such, in some embodiments, prongs 308, 310 and jaws 312, 314 together define a substantially circular shape. Alternatively, jaws 312, 314 may each include a different radius of curvature (not specifically shown). In certain embodiments, radius of curvature "R2" defined by jaws 312, 314 may be greater than or less than radius of curvature "R1" defined by prongs 308, 310. Accordingly, in certain embodiments, prongs 308, 310 and jaws 312, 314 together may define a substantially oblong shape. Alternatively, in other embodiments, jaws 312, 314 may be linear and instead include an angle (not specifically shown) therebetween. Accordingly, in other embodiments, prongs 308, 310 and jaws 312, 314 together define a substantially quadrilateral shape.

With additional reference to FIG. 3B, second ends 312b, 314b of jaws 312, 314, each include an end tip 312c, 314c, respectively. End tips 312c, 314c are rounded such that drape 30 is not punctured or marred while excess portion 30a of drape 30 is captured, located, and released from between second ends 312b, 314b of jaws 312, 314. In some embodiments, end tips 312c, 314c may each include a coating 313, 315 configured to prevent second ends 312b, 314b of jaws 312, 314 from damaging drape 30. In certain embodiments, coatings 313, 315 may include polymers, such as, for example, rubber, silicone, and/or polyvinyl chloride (PVC). In other embodiments, coatings 313, 315 may include a variety of alternative materials as necessary for its intended purpose. It is further contemplated that the coatings 313, 315 may be replaced by end caps or the like.

With reference to FIGS. 4, 5A, and 5B, additional embodiments of drape management assembly 300 are shown generally as drape management assembly 400 and drape management assembly 500, respectively. Drape management assemblies 400, 500 are substantially similar to drape management assembly 300 detailed above. As such, only additional and alternative features of drape management assemblies 400, 500 will be described below.

With specific reference to FIG. 4, drape management assembly 400 generally includes a base portion 402 and a grasping portion 404 pivotally or hingedly coupled to base portion 402. Similar to base portion 302, base portion 402 includes a stem 406 and a first and second prong 408, 410 extending therefrom. Grasping portion 404 of drape management assembly 400 includes a first jaw 412 and a second jaw 414, wherein in a first configuration, prongs 408, 410 and jaws 412, 414 define a cavity "E" therebetween. Similar to cavity "C1" (see FIG. 3A) described above with reference to the first configuration of drape management assembly 300, cavity "E" is also configured to capture and locate excess portion 30a of drape 30 (see FIG. 2).

Jaws 412, 414 of drape management assembly 400 each include a first end 412a, 414a and a second end 412b, 414b, respectively, wherein first ends 412a, 414a of jaws 412, 414 are coupled to prongs 408, 410 in a manner similar to which was described above with reference to jaws 312, 314 of drape management assembly 300. Second ends 412b, 414b of jaws 412, 414 are spaced apart a distance indicated by "D4," and each include a lip 413, 415, respectively. Lips 413, 415 extend away from cavity "E" and are spaced apart a distance indicated by "D5" between an end portion 413, 415, respectively thereof, wherein distance "D5" between end portions 413, 415 is greater than distance "D4" between second ends 412b, 414b of jaws 412, 414. It is contemplated that distance "D5" between end portions 413a, 415a of lips 413, 415 enables a clinician to feed excess portion 30a of drape 30 into cavity "E" while drape management assembly 400 is still in the first configuration, as illustrated in FIG. 4.

Lip 413 of drape management assembly 400 extends angularly away from cavity "E" in a manner in which lip 413 and second end 412b of first jaw 412 define an angle "α1" therebetween. Similarly, lip 415 of drape management assembly 400 extends angularly away from cavity "E" in a manner in which lip 415 and second end 414b of second jaw 414 define an angle "α2" therebetween. In some embodiments, angles "α1," "α2" between lips 413, 415 and second ends 412b, 414b, respectively, is less than 90 degrees. In certain embodiments, angles "α1," "α2" between lips 413, 415 and second ends 412b, 414b, respectively, may be approximately 90 degrees (not specifically shown) such that lips 413, 415 are parallel to a longitudinal axis "X" of drape management assembly 400.

With specific reference to FIG. 5A, drape management assembly 500 generally includes a base portion 502 and a grasping portion 504 pivotally or hingedly coupled to base portion 502. Similar to base portions 302, 402, base portion 502 includes a stem 506 and a first and second prong 508, 510 extending therefrom. Grasping portion 504 of drape management assembly 500 includes a first jaw 512 and a second jaw 514, wherein in a first configuration, prongs 508, 510 and jaws 512, 514 define a cavity "F" therebetween. Similar to cavities "C1," "E" (see FIGS. 3A and 4) described above with reference to the first configuration of respective drape management assembly 300, 400, cavity "F" is also configured to capture and locate excess portion 30a of drape 30.

Jaws 512, 514 each include a first end 512a, 514a and a second end 512b, 514b, respectively, wherein first ends 512a, 514a of jaws 512, 514 are pivotally or hingedly coupled to prongs 508, 510 in a manner similar to which was described above with reference to jaws 312, 314, 412, 414. Second ends 512b, 514b of jaws 512, 514 are spaced apart a distance indicated by "D6," and each include a lip 513, 515, respectively. Lips 513, 515 extend angularly towards cavity "F" and are spaced apart a distance indicated by "D7" between a first end portion 513a, 515a, respectively thereof, wherein distance "D6" between second ends 512b, 514b of jaws 512, 514 is greater than distance "D7" between first end portions 513a, 515a of lips 513, 515.

It is contemplated that distance "D6" between second ends 512b, 514b of jaws 512, 514 is sized and configured to enable a clinician to feed excess portion 30a of drape 30 into cavity "F" while drape management assembly 500 is still in the first configuration, as illustrated in FIG. 5A. Similar to distance "D4" between second ends 412b, 414b of jaws 412, 414, distance "D7" between first end portions 513a, 515a of lips 513, 515 is configured to enable excess portion 30a of drape 30 to be incrementally released from within cavity "F" as necessary to maintain full range of motion for robotic arms 2, 3 and robotic surgical assemblies 100 coupled thereto while remaining within the sterile enclosure of drape 30.

Specifically, lip 513 of drape management assembly 500 extends angularly toward cavity "F" in a manner in which lip 513 and second end 512b of first jaw 512 define an angle "β1" therebetween. Similarly, lip 515 extends angularly toward cavity "F" in a manner in which lip 515 and second end 514b of second jaw 514 define an angle "β2" therebetween. In some embodiments, angle "β1," "β2" between lip 513, 515 and end 512b, 514b, respectively, is greater than 90 degrees. In certain embodiments, angle "β1," "β2" between lip 513, 515 and end 512b, 514b, respectively, is approximately 90 degrees (not specifically shown) such that lip 513, 515 is parallel to a longitudinal axis "Y" of drape management assembly 500. It is envisioned that angle "β1," "β2" between lip 513, 515 and end 512b, 514b, respectively, is inversely proportional to distance "D7" between first end portions 513a, 515a of lips 513, 515. Due to the angular extension of lips 513, 515 towards cavity "F," first end portions 513a, 515a of lips 513, 515 engage excess portion 30a of drape 30 located within cavity "F" such that the entire excess slack or excess portion 30a of drape 30 is unable to be released at once or is inhibited from being released.

With reference to FIG. 5B, in another embodiment of drape management assembly 500, each lip 513, 515 includes a second end portion 513b, 515b, respectively. Second end portions 513b, 515b are each pivotally or hingedly coupled to second ends 512b, 514b of jaws 512, 514 via a hinge 517, 519, respectively. In some embodiments, hinges 517, 519 are resiliently biased in a direction indicated by arrows "G1," "G2," respectively, such that lips 513, 515 rotate about hinges 517, 519 relative to jaws 512, 514 to an approximated position. In certain embodiments, hinges 517, 519 each include a stop member 517a, 519a, respectively. Stop members 517a, 519a are configured to prevent rotation of lips 513, 515 beyond a threshold such that first end portions 513a, 515a of lips 513, 515 always maintain a minimum spaced apart distance "D7."

In this embodiment, when a clinician feeds excess portion 30a of drape 30 into cavity "F," lips 513, 515 of drape management assembly 500 are configured to rotate about hinges 517, 519, towards jaws 512, 514 (or away from one another), respectively, against the bias of hinges 517, 519. Such a rotation of lips 513, 515 enlarges distance "D7" between first end portions 513a, 515a of lips 513, 515 such that excess portion 30a of drape 30 may more easily be fed into cavity "F" of drape management assembly 500. Similar to the embodiment of drape management assembly 500 described with reference to FIG. 5A, the minimum distance "D7" between first end portions 513a, 515a of lips 513, 515 is configured to enable excess portion 30a of drape 30 to be incrementally released from within cavity "F" as necessary to maintain full range of motion for robotic arms 2, 3 and robotic surgical assemblies 100 coupled thereto while remaining within the sterile enclosure of drape 30.

In operation, turning back to FIGS. 1-3B, with drape management assembly 300 in a first configuration (see FIG. 3A), a clinician rotates jaws 312, 314 about hinges 316, 318 in the directions indicated by arrows "B1," "B2" until hinge locks (not shown) selectively fix jaws 312, 314 into the second configuration (see FIG. 3B). Robotic arms 2, 3 and robotic surgical assemblies 100 coupled thereto are then enclosed within drape 30 (see FIGS. 1 and 2) and excess portion 30a of drape 30 is gathered and fed into cavity "C2" between prongs 308, 310 and jaws 312, 214 of drape management assembly 300. The clinician then disengages the hinge locks such that jaws 312, 314 are resiliently biased by hinges 316, 318 in the direction indicated by arrows "A1," "A2" to the first configuration shown in FIG. 3A. After excess portion 30a of drape 30 is located and captured within cavity "C1" between prongs 308, 310 and jaws 312, 214, the clinician proceeds with the medical procedure.

During the medical procedure, excess portion 30a of drape 30 is incrementally released from within cavity "C1" through distance "D2" between second ends 312b, 314b as necessary to enable full range of motion for robotic arms 2, 3 and robotic surgical assemblies 100 coupled thereto. If excess portion 30a of drape 30 reaccumulates, the clinician repeats the process of gathering excess portion 30a of drape 30 and locating it within cavity "C1" until the medical procedure is completed.

The operation of drape management assemblies 400, 500 are substantially similar to the operation of drape management assembly 300. However, as noted above, in the operation of drape management assemblies 400, 500, the clinician may more easily feed excess portion 30a of drape 30 directly into cavities "E," "F," respectively, while drape management assemblies 400, 500 are in the first configuration, as illustrated in FIGS. 4 and 5A.

It will be understood that various modifications may be made to the embodiments disclosed herein. For example, in certain embodiments, drape management assemblies 300, 400, 500 may also be configured to route cables and wires (not specifically shown) through cavities "C1," "E," and "F," respectively, such that the cables and wires do not interfere with the medical procedure. Therefore, the above description should not be construed as limiting, but merely as exemplifications of various embodiments. Those skilled in the art will envision other modifications within the scope and spirit of the claims appended thereto.

The invention claimed is:

1. A robotic surgical system, comprising:
   at least one robotic arm;
   a robotic surgical assembly supported on each robotic arm;
   an electromechanical surgical instrument connected to each robotic surgical assembly, wherein the electromechanical surgical instrument is controlled by the respective robotic surgical assembly; and
   a drape management assembly supported on each robotic surgical assembly, wherein each drape management assembly includes:
      a base portion configured for connection to the robotic surgical assembly, wherein the base portion includes a first prong and a second prong; and
      a grasping portion extending from the base portion, the base portion and the grasping portion defining a cavity therebetween, wherein the cavity is configured to locate an excess portion of a drape which sheaths at least the robotic arm of the robotic surgical system, wherein the grasping portion includes a first jaw and second jaw each rotatably coupled to a respective one of the first prong and the second prong of the base portion, wherein in a first configuration, the first and second jaws are approximated and wherein in a second configuration, the first and second jaws are spaced apart.

2. The robotic surgical system according to claim 1, wherein the first and second jaws of the drape management assembly are resiliently biased to rotatably return to the first configuration.

3. The robotic surgical system according to claim 2, wherein each of the first and second jaws of the drape management assembly includes a first and second end, respectively, wherein the first end of each of the first and second jaws is hingedly coupled to the first and second prongs, respectively.

4. The robotic surgical system according to claim 3, wherein in the first configuration of the drape management assembly, the second ends of the first and second jaws are spaced apart a first distance, and wherein in the second configuration of the drape management assembly, the second ends of the first and second jaws are spaced apart a second distance greater than the first distance.

5. The robotic surgical system according to claim 4, wherein in the first configuration of the drape management assembly, the first distance between the second ends of the first and second jaws is configured to incrementally release the excess portion of the drape from within the cavity formed by the base portion and the grasping portion.

6. The robotic surgical system according to claim 4, wherein in the second configuration of the drape management assembly, the second distance between the second ends of the first and second jaws is configured for gathering and locating the excess portion of the drape within the cavity formed by the base portion and the grasping portion such that the excess portion of the drape is located and captured within the cavity formed by the base portion and the grasping portion when the first and second jaws are returned to the first configuration of the drape management assembly.

7. The robotic surgical system according to claim 3, wherein the second ends of the first and second jaws of the drape management assembly each include a first and second lip, respectively, wherein each of the first and second lips includes an end portion extending away from the second ends of the first and second jaws.

8. The robotic surgical system according to claim 7, wherein the first and second lips of the drape management assembly extend away from the cavity formed by the base portion and the grasping portion and away from one another, such that a distance between the end portions of the first and second lips is greater than a distance between the second ends of the first and second jaws.

9. The robotic surgical system according to claim 7, wherein the first and second lips of the drape management assembly extend towards the cavity formed by the base portion and the grasping portion and towards one another, such that a distance between the end portions of the first and second lips is less than a distance between the second ends of the first and second jaws.

10. The robotic surgical system according to claim 9, wherein the first and second lips of the drape management assembly are hingedly coupled to the second ends of the first and second jaws respectively, and resiliently biased to an approximated position wherein the distance between the end portions of the first and second lips is less than the distance between the second ends of the first and second jaws.

11. The robotic surgical system according to claim 1, wherein the cavity of the drape management assembly includes a first cavity formed by the base portion and the grasping portion in the first configuration, and a second cavity formed by the base portion and the grasping portion in the second configuration, the second cavity being larger than the first cavity.

12. The robotic surgical system according to claim 1, wherein the first and second prongs of the drape management assembly each include a first radius of curvature and the first and second jaws each include a second radius of curvature.

13. The robotic surgical system according to claim 1, wherein the base portion of the drape management assembly further includes a stem supporting the first and second prongs.

14. A robotic surgical system, comprising:
at least one robotic arm;
a robotic surgical assembly supported on each robotic arm;
an electromechanical surgical instrument connected to each robotic surgical assembly, wherein the electromechanical surgical instrument is controlled by the respective robotic surgical assembly; and
a drape management assembly supported on each robotic surgical assembly, wherein each drape management assembly includes:
a base portion including:
a first prong having a first end and a second end; and
a second prong having a first end and a second end, the first and second prongs coupled to one another at the respective first ends thereof;
a grasping portion including:
a first jaw having a first end and a second end; and
a second jaw having a first end and a second end, the first ends of the first and second jaws operably coupled to the second ends of the first and second prongs, respectively, wherein the base portion and the grasping portion define a cavity therebetween, wherein the cavity is configured to locate an excess portion of a drape; and
a first hinge rotatably coupling the first prong and the first jaw and a second hinge rotatably coupling the second prong and the second jaw, the first and second hinges being spring loaded such that the first and second jaws are resiliently biased to a first configuration wherein the second ends of the first and second jaws are approximated towards one another, and wherein the second ends of the first and second jaws are deflectable apart from one another against the resilient bias of the first and second jaws.

15. The robotic surgical system according to claim 14, wherein the drape is configured to enclose a respective robotic arm of the robotic surgical system, and the drape management assembly is configured to incrementally release the excess drape portion such that the robotic arm maintains a full range of motion while sheathed by the drape.

16. The robotic surgical system according to claim 14, wherein the base portion of the drape management assembly includes a stem having a threaded portion configured to threadably couple the drape management assembly to a respective robotic surgical assembly of the robotic surgical system.

* * * * *